(12) United States Patent
Huang et al.

(10) Patent No.: US 10,905,559 B2
(45) Date of Patent: Feb. 2, 2021

(54) MAGNETIC LOCKING MECHANISM (MLM) FOR JOINT ARTHROPLASTY

(71) Applicant: Magnetic Joints LLC, Burien, WA (US)

(72) Inventors: Brandi Huang, Issaquah, WA (US); Jerry Huang, Issaquah, WA (US)

(73) Assignee: Magnetic Joints LLC, Burien, WA (US)

( * ) Notice: Subject to any disclaimer, the term of this patent is extended or adjusted under 35 U.S.C. 154(b) by 0 days.

(21) Appl. No.: 16/669,300

(22) Filed: Oct. 30, 2019

(65) Prior Publication Data

US 2020/0129299 A1 Apr. 30, 2020

Related U.S. Application Data

(60) Provisional application No. 62/752,347, filed on Oct. 30, 2018.

(51) Int. Cl.
*A61F 2/38* (2006.01)
*A61F 2/46* (2006.01)
*A61F 2/30* (2006.01)

(52) U.S. Cl.
CPC .......... *A61F 2/3804* (2013.01); *A61F 2/4605* (2013.01); *A61F 2002/30331* (2013.01); *A61F 2002/30451* (2013.01); *A61F 2002/3827* (2013.01); *A61F 2002/4698* (2013.01); *A61F 2310/00029* (2013.01)

(58) Field of Classification Search
CPC .. A61F 2/38; A61F 2/3804; A61F 2002/3809; A61F 2002/3827; A61F 2002/4698
USPC ........................... 623/20.22–20.13
See application file for complete search history.

(56) References Cited

U.S. PATENT DOCUMENTS

| 4,209,905 | A | 7/1980 | Gillings |
| 4,530,663 | A | 7/1985 | Portnoy |
| 8,206,459 | B1 * | 6/2012 | Lock .......................... A61F 2/80 623/33 |
| 8,568,457 | B2 | 10/2013 | Hunziker |
| 9,179,938 | B2 | 11/2015 | Pool et al. |

(Continued)

FOREIGN PATENT DOCUMENTS

WO 2017172566 A1 10/2017

*Primary Examiner* — Bruce E Snow
(74) *Attorney, Agent, or Firm* — Greenberg Traurig, LLP; David J. Dykeman; Roman Fayerberg

(57) ABSTRACT

A method of implanting a joint prosthesis assembly for joint arthroplasty using a coupling mechanism is disclosed. The method includes exposing a joint of a patient, resecting a portion of the joint, inserting a second prosthesis of the joint prosthesis assembly into a medullary canal, and inserting a first prosthesis of the joint prosthesis assembly from a lateral side of the joint. The joint prosthesis assembly includes a magnet. The magnet is configured to lock the first prosthesis of the joint prosthesis assembly to the second prosthesis of the joint prosthesis assembly. The first prosthesis of the joint prosthesis assembly includes a recess. The second prosthesis of the joint prosthesis assembly includes a protrusion. The recess is configured to house the protrusion. Alternatively, the first prosthesis and the second prosthesis may be assembled in a direct line using the magnet for secure coupling of the components.

12 Claims, 7 Drawing Sheets

(56) References Cited

U.S. PATENT DOCUMENTS

| | | | |
|---|---|---|---|
| 9,744,056 B2* | 8/2017 | Kuiken | A61F 2/7812 |
| 2007/0105067 A1* | 5/2007 | Hayashi | A61C 8/0048 |
| | | | 433/172 |
| 2014/0277524 A1* | 9/2014 | Brownhill | A61F 2/3804 |
| | | | 623/20.11 |
| 2015/0005886 A1* | 1/2015 | Pinneo | A61F 2/32 |
| | | | 623/18.12 |
| 2015/0257860 A1 | 9/2015 | Andreen | |
| 2017/0256183 A1* | 9/2017 | Itagaki | G09B 23/34 |

\* cited by examiner

Fig. 4A
Fig. 4B
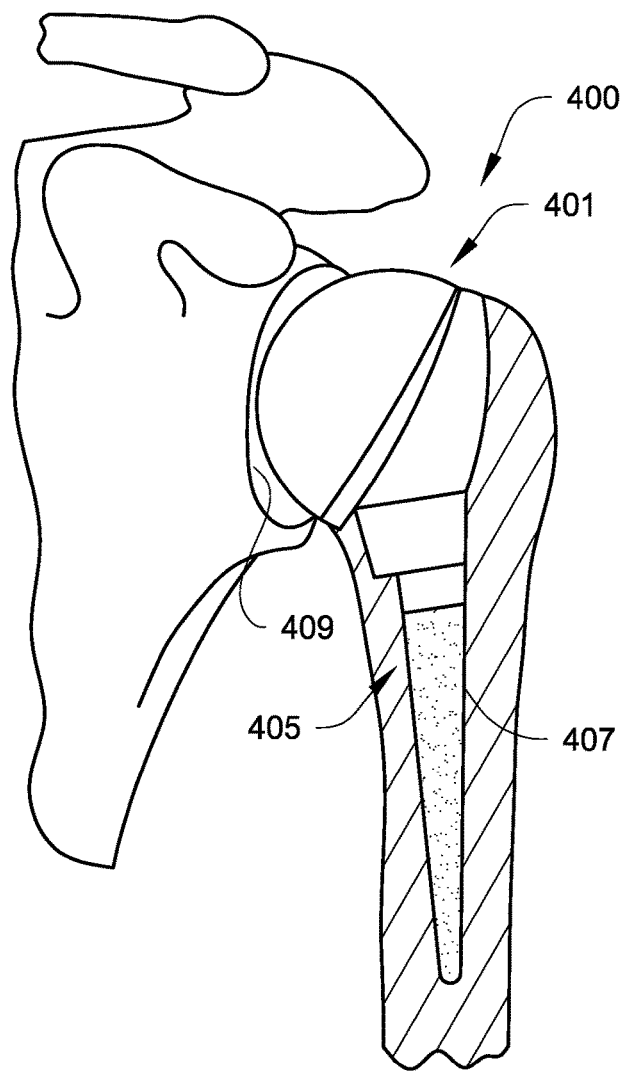
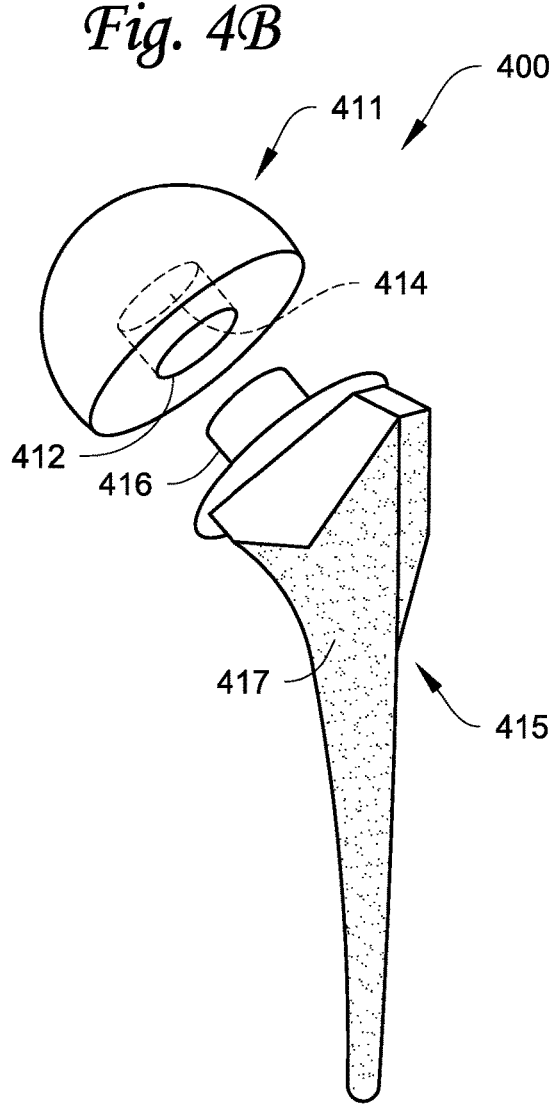

MAGNETIC LOCKING MECHANISM (MLM) FOR JOINT ARTHROPLASTY

FIELD OF THE DISCLOSURE

The present disclosure is generally related to an implantable joint prosthesis assembly for joint arthroplasty, e.g., a magnetic locking mechanism for joint arthroplasty modular components.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

A number of mechanisms may be used for coupling head and stem components in joint arthroplasty procedures, the most common being the Morse taper mechanism, which typically requires a wide exposure of a subject joint to allow for a direct line for tamping of the head onto the stem. However, this kind of wide exposure is not always possible. For example, in the case of radial head arthroplasty, the capitellum may interfere with a direct line access to the radial head. In revision surgery with extensive scar tissue, this can become even more challenging. In addition, the direct impaction of the head onto the stem may have inherent risk of iatrogenic fracture in the patient or damage to the prosthesis, and there is no mechanism for assessing the locking of the head to the stem. Furthermore, if the articulation of the prosthesis is off or loosens or dislodges, progressive loosening may occur with ultimate complete disarticulation. Alternatively, the Morse taper assembly may be performed outside the joint, but doing so requires the surgeon to then insert the entire assembly as one large component. The Morse taper mechanism fails to meet certain needs of the industry as it is not appropriate for minimally invasive joint arthroplasty.

SUMMARY

In at least one example embodiment, an implantable joint prosthesis assembly for joint arthroplasty includes a first prosthesis having a recess, a second prosthesis having a protrusion, and a magnetic prosthesis configured to connect the first prosthesis to the second prosthesis. The recess is configured to house the protrusion. The magnetic prosthesis is disposed between the first prosthesis of the joint prosthesis assembly and the second prosthesis of the joint prosthesis assembly.

In at least one other example embodiment, a method of implanting a joint prosthesis assembly for joint arthroplasty includes exposing a joint of a patient, resecting a portion (e.g., head) of the joint, inserting a second prosthesis of the joint prosthesis assembly into a medullary canal, and inserting a first prosthesis of the joint prosthesis assembly from a lateral side of the joint. In accordance with such example embodiment, the joint prosthesis assembly includes a magnet that is configured to lock the first prosthesis to the second prosthesis. Further, the first prosthesis includes a recess, the second prosthesis includes a protrusion, and the recess is configured to house the protrusion.

Embodiments disclosed herein provide reliable and reproducible locking of two modular components of a joint prosthesis assembly in joint arthroplasty. The embodiments allow for two modular components of a joint prosthesis assembly to be locked in a small anatomic space, thus providing a joint prosthesis assembly to be biocompatible and safely inserted and utilized inside a patient's anatomy. Also embodiments disclosed herein provide a joint prosthesis assembly that is easy to apply while avoiding human error when coupling prosthetic components of the joint prosthesis assembly. Accordingly, at least some of the embodiments disclosed herein advantageously fill industrial needs by providing an implant coupling mechanism that is strong, durable, easy to use, and reproducible in a surgeon's hands.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

The present disclosure provides a detailed and specific description that refers to the accompanying drawings. The drawings and specific descriptions of the drawings, as well as any specific or alternative embodiments discussed, are intended to be read in conjunction with the entirety of this disclosure. The magnetic locking mechanism in a joint prosthesis assembly for joint arthroplasty modular components may, however, be embodied in many different forms and should not be construed as being limited to the embodiments set forth herein; rather, these embodiments are provided by way of illustration only and so that this disclosure will be thorough, complete and fully convey understanding to those skilled in the art.

References are made to the accompanying drawings that form a part of this disclosure and which illustrate embodiments in which the systems and methods described in this specification may be practiced.

Figure 1:
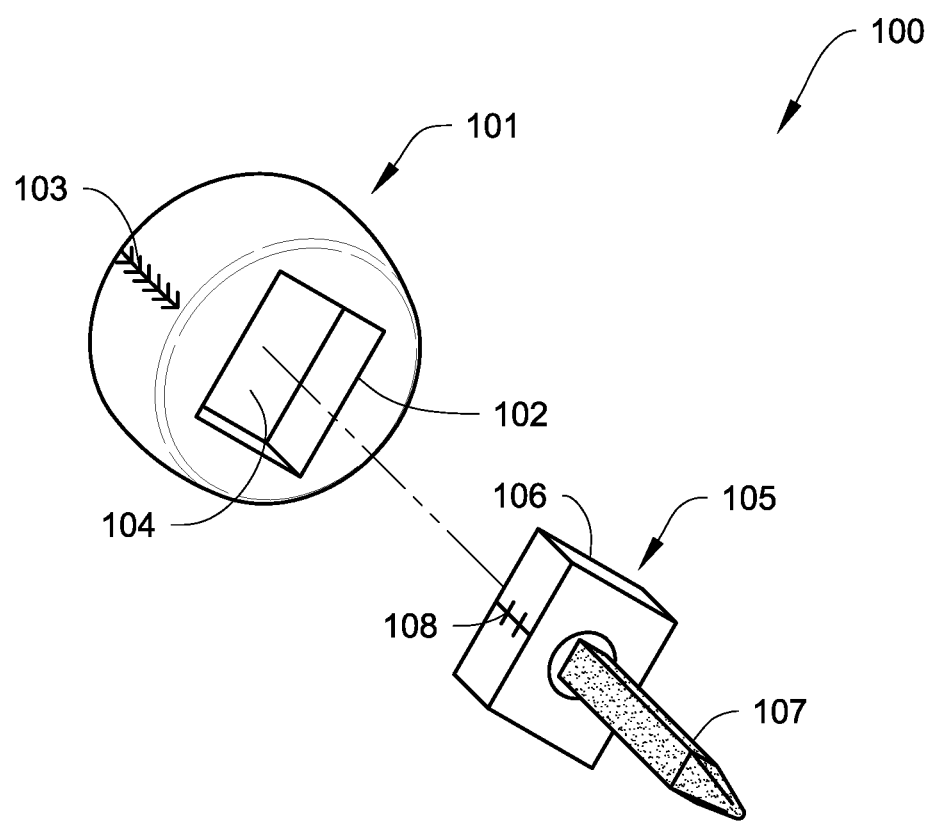

FIG. 1 shows an implantable joint prosthesis assembly for joint arthroplasty having a first prosthesis 101 with a recess and a second prosthesis with a protrusion, according to at least one example embodiment described herein.

Figure 2A:
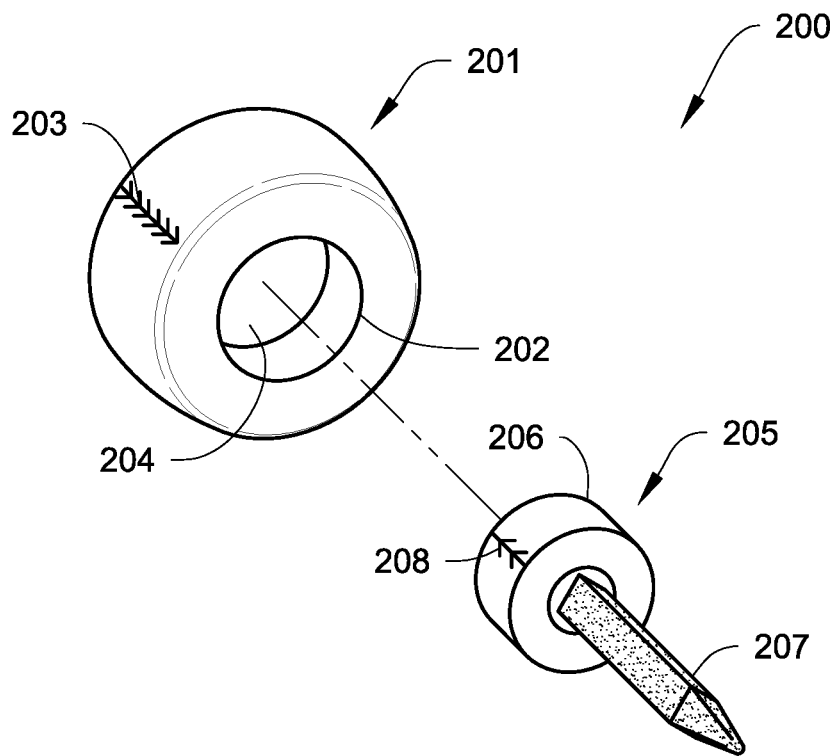
Figure 2B:
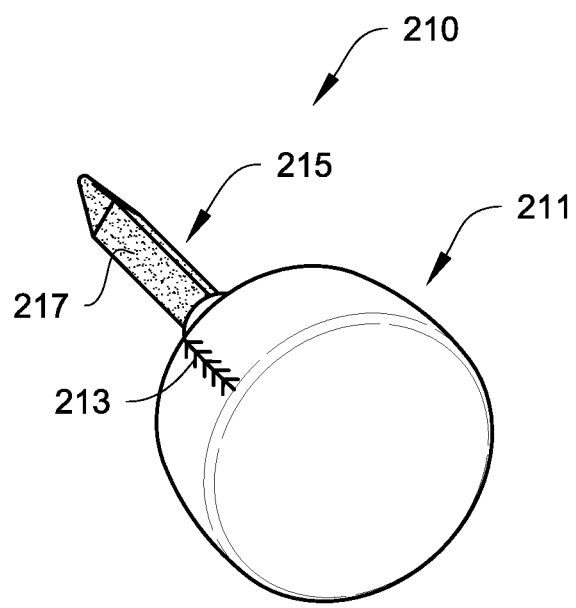
Figure 2C:
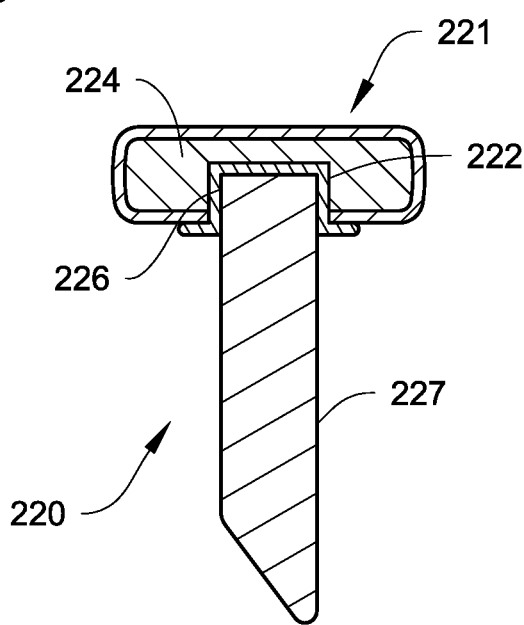

FIGS. 2A-2C show implantable joint prosthesis assemblies for joint arthroplasty, according to at least some embodiments described herein.

Figure 3:
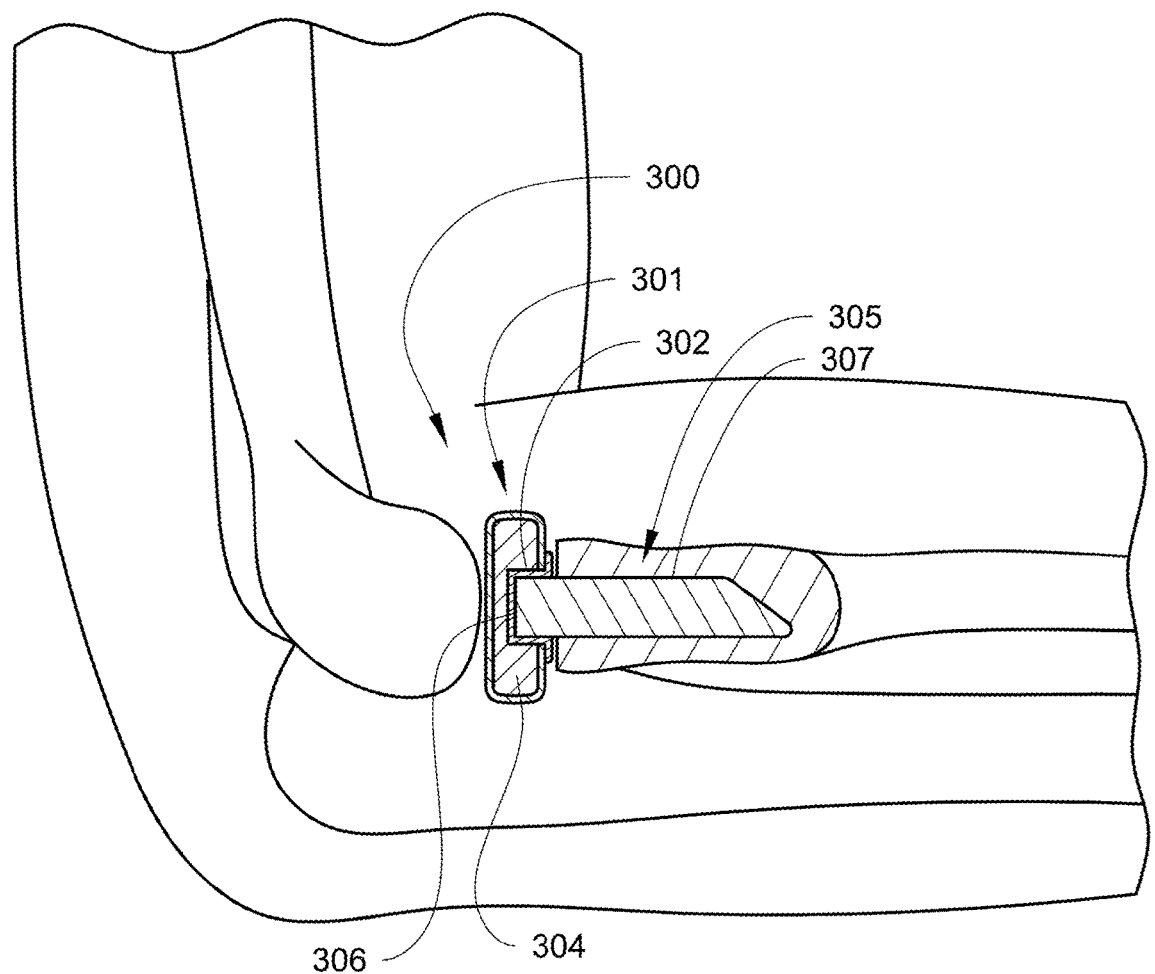

FIG. 3 shows a joint prosthesis assembly for joint arthroplasty implanted in an elbow joint, according to at least some embodiments described herein.

FIGS. 4A-4B show implantable joint prosthesis assemblies for shoulder arthroplasty, according to at least some embodiments described herein.

Figure 5A:
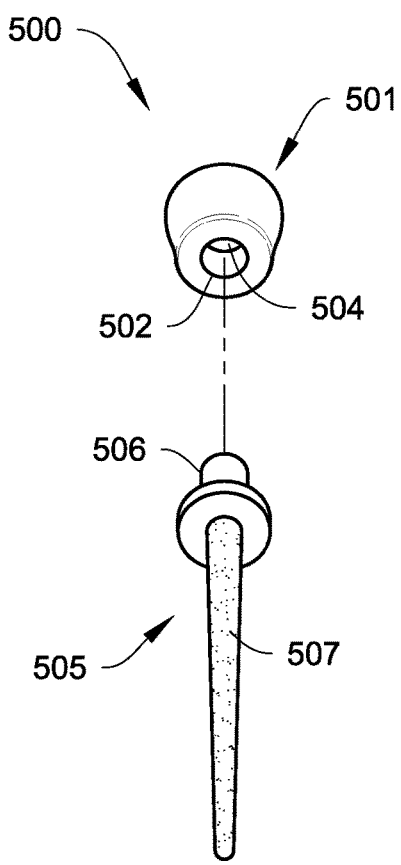
Figure 5B:
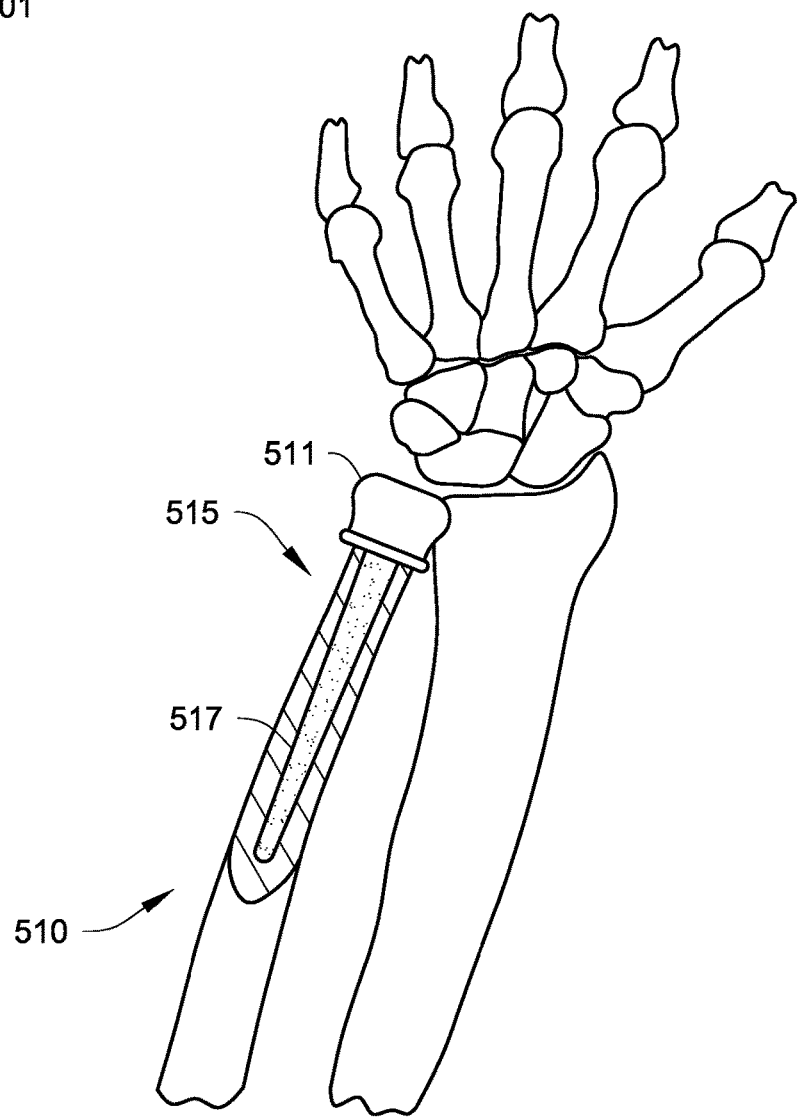

FIGS. 5A-5B show implantable joint prosthesis assemblies for ulnar arthroplasty, according to at least some embodiments described herein.

Figure 6A:
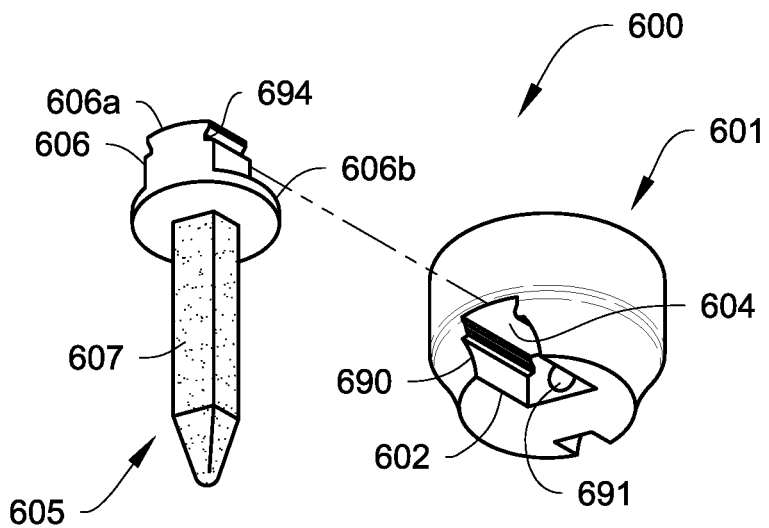
Figure 6B:
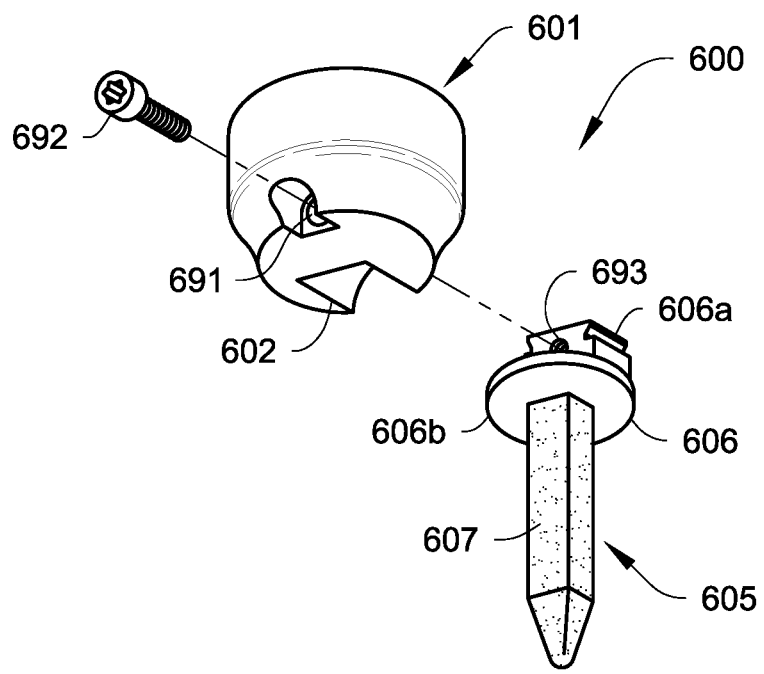
Figure 6C:
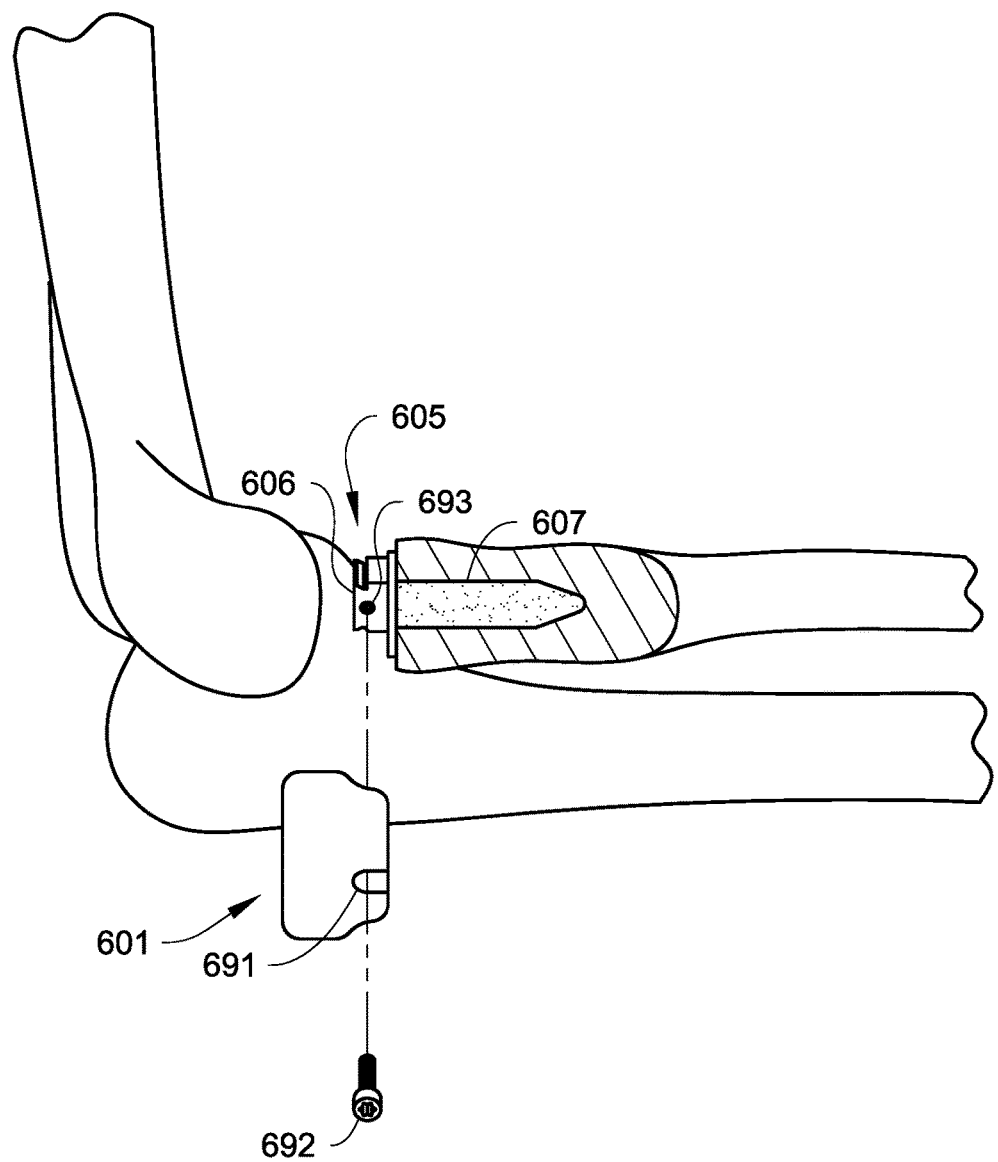

FIGS. 6A-6C show implantable joint prosthesis assemblies for joint arthroplasty having a side loading mechanism with a screw locking mechanism, according to at least some embodiments described herein.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a", "an" and "the" include plural references unless the context clearly dictates otherwise. Although any systems and methods similar or equivalent to those described herein may be used in the practice or testing of embodiments of the present disclosure, the preferred, systems and methods are now described.

Embodiments of the present disclosure will be described more fully hereafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

FIG. 1 shows an implantable joint prosthesis assembly 100 for joint arthroplasty having a first prosthesis 101 with a recess 102 and a second prosthesis 105 with a protrusion 106, according to at least one example embodiment described herein. In at least one embodiment, the first prosthesis 101 may be a radial head prosthesis that includes a recess 102. The recess 102 may be of any suitable size to fit within the first prosthesis 101 and/or any shape suitable (square, rectangle, circle, ellipse, triangle, cube, cuboid, spherical, half-spherical, prism, etc.) to match the shape of the protrusion 106 of the second prosthesis 105. As shown in the example embodiment of FIG. 1, the recess 102 is a pillar shape with a square opening. The first prosthesis 101 also includes a marker 103 for alignment with the second prosthesis 105. The first prosthesis 101 may include any durable and/or composite materials such as chrome, pyrocarbon, cobalt-chrome alloy, other metal alloy, etc., suitable to extend the lifespan of the implantable.

In at least one example embodiment, the second prosthesis 105 may be a prosthetic stem and/or a radial stem that includes a stem portion 107 and a protrusion 106. The second prosthesis 105 may include, e.g., a rough grit-blast material. It will be appreciated that grit-blast material promotes bony on-growth and facilitates osseous integration. The second prosthesis 105 may have a plasma coating or may be a polished smooth stem. Further, the stem portion 107 of the second prosthesis 105 may be of any suitable shape (straight, fluted, curved, etc.) and may be of any suitable/varying lengths and/or any sizes suitable to match the shape/length/size of the canal of the joint where the stem portion 107 may be inserted. The protrusion 106 may be a collar and/or a peg. The protrusion 106 may include any suitable ferromagnetic metal(s).

The joint prosthesis assembly 100 may also include a magnetic prosthesis 104 that may be or include rare-earth magnet(s). It will be appreciated that rare-earth elements are metals that are ferromagnetic and may be magnetized to become permanent magnets; that rare-earth magnets refer to strong permanent magnets made from alloys of rare-earth elements; and that rare-earth magnets may be the strongest type of permanent magnets, producing significantly stronger magnetic fields than other types such as ferrite or alnico magnets. For example, a magnetic field typically produced by rare-earth magnets may exceed 1.4 teslas, whereas ferrite or ceramic magnets typically exhibit fields of 0.5 to 1 tesla. The magnetic prosthesis 104 may include at least one of the two types of rare-earth magnets: neodymium magnets and samarium-cobalt magnets. Stronger rare-earth magnets may allow smaller magnets to be incorporated into existing prosthetic joint designs. Larger sizes would be necessary with traditional magnets, limiting their incorporation into prosthetic joint designs. The neodyminum, specifically N-52, is the strongest commercially available magnet.

Rare-earth magnets may be extremely brittle and also vulnerable to corrosion, so they are typically plated or coated to prevent breaking, chipping, or crumbling into powder. For use in a joint prosthesis assembly, rare-earth magnets are utilized in at least some of the example embodiments described herein to promote bony on-growth.

The magnetic prosthesis 104 may be inserted inside the first prosthesis 101. That is, the magnetic prosthesis 104 may be inserted into any head of a prosthesis with suitable shape and/or size. In at least one example embodiment, the magnetic prosthesis 104 is inserted in the recess 102. In at least one other example embodiment, the magnetic prosthesis 104 is inserted in the first prosthesis 101 and the recess 102 is formed in the magnetic prosthesis 104 (see e.g., FIG. 2C). The recess 102 may be disposed at any location (e.g., in the middle) on the first prosthesis 101 or on the magnetic prosthesis 104 suitable to match the location of the protrusion 106 of the second prosthesis 105 relative to the joint prosthesis assembly 100.

The protrusion 106 may be shaped to couple the recess 102 of the first prosthesis 104. For example, the magnetic prosthesis 104 may be inserted in the recess 102, or the recess 102 may be formed in the magnetic prosthesis 104. The shape and/or size of the protrusion 106 may match the shape and/or size of the recess 102 to facilitate, e.g., the magnetic prosthesis 104 being inserted in the recess 102 or the recess 102 being formed in the magnetic prosthesis 104. The first prosthesis 101 and the second prosthesis 105 are connected by the polarity of the rare-earth magnet pulling the ferromagnetic metal into the recess 102. The protrusion 106 (e.g., a collar and/or a peg) of the second prosthesis 105 may articulate with the first prosthesis 101.

In an operation, once the protrusion 106 is engaged into the recess 102, with the magnetic prosthesis 104 being inserted in the recess 102 or the recess 102 being formed in the magnetic prosthesis 104, a magnetic bond may be formed and the protrusion 106 may be pulled into the recess 102 by the magnetic forces. In another embodiment, the magnetic prosthesis 104 may be disposed on the protrusion 106 and coupled into the recess 102 of the first prosthesis 101. In such embodiment, the first prosthesis 101 may include ferromagnetic metal(s) to create a magnetic bond between the protrusion 106 (where the magnetic prosthesis 104 is disposed) and the first prosthesis 101.

In FIG. 1, the square shape of the recess 102 and the square shape of the protrusion 106 may prevent radial rotation of the first prosthesis 101 relative to the second prosthesis 105 in clinical situations. The marker 103 on the first prosthesis 101 and the marker 108 on the second prosthesis 105 are provided to, e.g., ensure proper alignment during an implant procedure. For example, during the implant procedure, when the first prosthesis 101 and the second prosthesis 105 are assembled, e.g., when the protrusion 106 is inserted into the recess 102 and/or the magnetic prosthesis 104 locks the first prosthesis 101 and the second prosthesis 105, if the marker 103 and the marker 108 are on a same line in a axial direction, the first prosthesis 101 is aligned with the second prosthesis 105. If the marker 103 and the marker 108 are not on a same line in the axial direction, adjustments need to be made (e.g., via an alignment tool (not shown)) to ensure the first prosthesis 101 is aligned with the second prosthesis 105.

In accordance with the magnetic locking mechanism disclosed herein, loosening may not occur as magnets have an average lifespan of about 100 years. Any temporary minor separation of the magnet from the ferromagnetic metal would immediately lock back in place from the pull of the magnet against the ferromagnetic metal.

In at least one example embodiment, the magnetic locking mechanism in the implantable joint prosthesis assembly 100 for joint arthroplasty may include the magnetic prosthesis 104 (e.g., magnet(s) such as rare-earth magnet(s)) that may be coupled to the first prosthesis 101 (e.g., ferromagnetic metal(s)), and/or the second prosthesis 105 (e.g., ferromagnetic metal(s)) used in joint arthroplasty.

In at least one other example embodiment, the magnetic prosthesis 104 may be disposed/inserted in the first prosthesis 101 (e.g., a radial head) or the second prosthesis 105 (e.g., a radial stem) or the protrusion 106 (e.g., collar and/or peg, etc.) of the second prosthesis 105.

In at least one other example embodiment, the magnetic prosthesis 104 may be connected to the first prosthesis 101 (e.g., a ferromagnetic metal head) and/or the second prosthesis 105 (e.g., a ferromagnetic metal stem) by its polarity, and/or may be directly welded into the first prosthesis 101 or the second prosthesis 105.

In the example embodiment of FIG. 1, the magnetic prosthesis 104 is welded into the first prosthesis 101 (e.g., a radial head). The composite radial head (first prosthesis 101 in which the magnetic prosthesis 104 is welded) may then be coupled to the second prosthesis 105 (e.g., a radial stem having a ferromagnetic metal collar and/or peg (of the protrusion 106)). By providing a recess 102 in the first prosthesis 101 (e.g., a radial head), the protrusion 106 (e.g., a metal collar and/or peg) may articulate tightly into the recess 102 in the first prosthesis 101 (e.g., a radial head) and form a magnetic bond with the magnetic prosthesis 104. The square shape of the recess 102 also allows for exact orientation of the first prosthesis 101 (e.g., a radial head) relative to the second prosthesis 105 (e.g., a radial stem).

In accordance with at least one example embodiment, the magnetic locking mechanism may include a magnet (e.g., a rare-earth magnet) inserted into a hollowed head prosthesis including a ferromagnetic metal. The composite head (head with magnet inserted) may articulate with a stem prosthesis (that includes a ferromagnetic metal). The magnet may be welded into the head prosthesis and then articulated with the stem prosthesis together.

In another example embodiment, the magnet may be part of the stem prosthesis either by a magnetic bond or welding. The composite magnetic stem (stem with magnet bond/welded) may then be articulated with a ferromagnetic metal head.

In yet another example embodiment, a magnetic collar and/or peg (of a protrusion including rare-earth magnet material) may be disposed on a prosthetic stem, and an augment (not shown) may be added to the collar and/or the peg that is ferromagnetic. For example, the augment may be a layer of coating. Embodiments disclosed herein may be used for radial head arthroplasty. However, it will be appreciated that the magnetic locking mechanism disclosed herein may also be used in other joints including total shoulder arthroplasty, wrist arthroplasty, ankle arthroplasty, small joint arthroplasty in the hands and feet, as well as knee and hip arthroplasty, etc. The magnet locking mechanism disclosed herein allows for any components of implant devices to be coupled easily with a secure and lasting bond and allows for ease of increasing modularity of current joint prosthetic designs as adding head, collar, peg, and/or stem components would be easier without complex design features (e.g., screw fixation).

FIGS. 2A-2C show implantable joint prosthesis assemblies 200, 210, and 220 for joint arthroplasty, according to some example embodiments. As shown in FIG. 2A, the joint prosthesis assembly 200 includes a first prosthesis 201 and a second prosthesis 205. The first prosthesis 201 includes a recess 202 and a marker 203.

The second prosthesis 205 includes a stem portion 207 and a protrusion 206. The joint prosthesis assembly 200 includes a magnetic prosthesis 204, which may be inserted or welded in the recess 202. In another example embodiment, the magnetic prosthesis 204 may be inserted or welded in the first prosthesis 201 and the recess 202 may be formed in the magnetic prosthesis 204 (see e.g., 222 and 224). In yet another example embodiment, the magnetic prosthesis 204 may be disposed on the protrusion 206 and coupled into the recess 202 of the first prosthesis 201. The marker 203 on the first prosthesis 201 and the marker 208 on the second prosthesis 205 may be utilized to ensure proper alignment during an implant procedure.

As shown in FIG. 2B, the assembled joint prosthesis assembly 210 includes a first prosthesis 211 and a second prosthesis 215. The first prosthesis 211 includes a recess (not shown). The first prosthesis 211 also includes a marker 213. The second prosthesis 215 includes a stem portion 217 and a protrusion (not shown). The joint prosthesis assembly 210 also includes a magnetic prosthesis (not shown). In at least one example embodiment, the magnetic prosthesis is inserted or welded in the recess. In another example embodiment, the magnetic prosthesis is inserted or welded in the first prosthesis 211 and the recess is formed in the magnetic prosthesis (see e.g., 222 and 224). In yet another example embodiment, the magnetic prosthesis may be disposed on the protrusion and coupled into the recess of the first prosthesis 211. The marker 213 on the first prosthesis 211 and a marker (not shown) on the second prosthesis 215 may be utilized to ensure proper alignment during an implant procedure.

FIG. 2C shows a cross-sectional view of the assembled joint prosthesis assembly 220, which includes a first prosthesis 221 and a second prosthesis 225. The first prosthesis 221 includes a recess 222 and a marker (not shown). The second prosthesis 225 includes a stem portion 227 and a protrusion 226. The joint prosthesis assembly 220 also includes a magnetic prosthesis 224, which may be inserted or welded in the first prosthesis 221, and the recess 222 may be formed in the magnetic prosthesis 224. The marker on the first prosthesis 221 and a marker (not shown) on the second prosthesis 225 may be utilized to ensure proper alignment during an implant procedure.

It will be appreciated that FIGS. 2A-2C pertains to embodiments similar to the embodiment of FIG. 1. For example, the structure and function of the first prosthesis, the recess, the marker of the first prosthesis, the magnetic prosthesis, the second prosthesis, the protrusion, the stem portion, and the marker of the second prosthesis in FIGS. 2A-2C are the same or similar to those of the first prosthesis, the recess, the marker of the first prosthesis, the magnetic prosthesis, the second prosthesis, the protrusion, the stem portion, and the marker of the second prosthesis in FIG. 1. However, as shown in FIGS. 2A and 2C, the recesses 202 and 222 are cylinder-shaped with a circular opening. The protrusions 206 and 226 (e.g., collar or peg) are also cylinder-shaped with a circular top surface, and match the size and shape of the recesses 202 and 222, respectively. The cylinder shape of the recesses/protrusions may facilitate radial rotation of the protrusions inside the recess. The stem portion 207 is a cylinder shape. The cylinder shape of the stem portion may facilitate radial rotation of the stem portion inside the canal of the joint where the stem portion is inserted. In FIGS. 2B and 2C, the stem portions 217 and 227 have a tapered (e.g., triangle-shaped) end. The tapered end may be made of e.g., titanium or any suitable material (that has low density and high strength and is resistant to corrosion), and may be used to aid insertion.

FIG. 3 shows a cross-sectional view of the joint prosthesis assembly 300 for joint arthroplasty implanted in an elbow joint, according to at least one example embodiment. The joint prosthesis assembly 300 includes a first prosthesis 301 and a second prosthesis 305. The first prosthesis 301 includes a recess 302 and a marker (not shown). The second prosthesis 305 includes a stem portion 307 and a protrusion 306. The joint prosthesis assembly 300 also includes a magnetic prosthesis 304. In at least one example embodiment, the magnetic prosthesis 304 is inserted or welded in the recess 302. In another example embodiment, the magnetic prosthesis 304 is inserted or welded in the first prosthesis 301 and the recess 302 is formed in the magnetic prosthesis 304. In yet another example embodiment, the magnetic prosthesis 304 may be disposed on the protrusion 306 and couple into the recess 302 of the first prosthesis 301. The marker on the first prosthesis 301 and a marker (not shown) on the second prosthesis 305 may be utilized to ensure proper alignment during an implant procedure.

It will be appreciated that FIG. 3 pertains to embodiments similar to the embodiments of FIGS. 1 and 2. For example, the structure and function of the first prosthesis, the recess, the marker of the first prosthesis, the magnetic prosthesis, the second prosthesis, the protrusion, the stem portion, and the marker of the second prosthesis in FIG. 3 are the same or similar to those of the first prosthesis, the recess, the marker of the first prosthesis, the magnetic prosthesis, the second prosthesis, the protrusion, the stem portion, and the marker of the second prosthesis in FIGS. 1 and 2.

FIGS. 4A and 4B show implantable joint prosthesis assemblies 400 and 410 for a total shoulder arthroplasty, according to at least some example embodiments. As shown in FIG. 4A, the assembled joint prosthesis assembly 400 (e.g., a total shoulder prosthesis) includes a first prosthesis 401 (e.g., a humeral head having a half-spherical shape) and a second prosthesis 405 (e.g., a humeral stem). The first prosthesis 401 includes a recess (not shown) and a marker (not shown). The second prosthesis 405 includes a stem portion 407 and a protrusion (not shown). The joint prosthesis assembly 400 also includes a magnetic prosthesis (not shown). In at least one example embodiment, the magnetic prosthesis is inserted or welded in the recess. In another example embodiment, the magnetic prosthesis is inserted or welded in the first prosthesis 401, and the recess is formed in the magnetic prosthesis. In yet another example embodiment, the magnetic prosthesis may be disposed on the protrusion and couple into the recess of the first prosthesis 401. The marker on the first prosthesis 401 and a marker (not shown) on the second prosthesis 405 may be utilized to ensure proper alignment during implant procedure. The joint prosthesis assembly 400 may also include a glenoid prosthesis 409.

In FIG. 4B, the joint prosthesis assembly 410 includes a first prosthesis 411 and a second prosthesis 415. The first prosthesis 411 includes a recess 412 and a marker (not shown). The second prosthesis 415 includes a stem portion 417 and a protrusion 416. The joint prosthesis assembly 410 also includes a magnetic prosthesis 414. In at least one example embodiment, the magnetic prosthesis 414 is inserted or welded in the recess 412. In another example embodiment, the magnetic prosthesis 414 is inserted or welded in the first prosthesis 411 and the recess 412 is formed in the magnetic prosthesis 414. In yet another example embodiment, the magnetic prosthesis 414 may be disposed on the protrusion 416 and coupled into the recess 412 of the first prosthesis 411. The marker on the first prosthesis 411 and the marker (not shown) on the second prosthesis 415 may be utilized to ensure proper alignment during an implant procedure.

It will be appreciated that FIGS. 4A and 4B pertain to embodiments similar to the embodiments of FIGS. 1-3. For example, the structure and function of the first prosthesis, the recess, the marker of the first prosthesis, the magnetic prosthesis, the second prosthesis, the protrusion, the stem portion, and the marker of the second prosthesis in FIGS. 4A and 4B are the same or similar to those of the first prosthesis, the recess, the marker of the first prosthesis, the magnetic prosthesis, the second prosthesis, the protrusion, the stem portion, and the marker of the second prosthesis in FIGS. 1-3.

FIGS. 5A and 5B show implantable joint prosthesis assemblies 500 and 510 for ulnar arthroplasty, according to at least some example embodiments. As shown in FIG. 5A, the joint prosthesis assembly 500 (e.g., an ulnar prosthesis) includes a first prosthesis 501 (e.g., an ulnar head) and a second prosthesis 505 (e.g., an ulnar stem). The first prosthesis 501 includes a recess 502 and a marker (not shown). The second prosthesis 505 includes a stem portion 507 and a protrusion 506. The joint prosthesis assembly 500 also includes a magnetic prosthesis 504. In at least one example embodiment, the magnetic prosthesis 504 is inserted or welded in the recess 502. In another example embodiment, the magnetic prosthesis 504 is inserted or welded in the first prosthesis 501, and the recess 502 is formed in the magnetic prosthesis 504. In yet another example embodiment, the magnetic prosthesis 504 may be disposed on the protrusion 506 and couple into the recess 502 of the first prosthesis 501. The marker on the first prosthesis 501 and the marker (not shown) on the second prosthesis 505 may be utilized to ensure proper alignment during an implant procedure.

In FIG. 5B, the assembled joint prosthesis assembly 510 (e.g., an ulnar prosthesis) includes a first prosthesis 511 (e.g., an ulnar head) and a second prosthesis 515 (e.g., an ulnar stem). The first prosthesis 511 includes a recess (not shown) and a marker (not shown). The second prosthesis 515 includes a stem portion 517 and a protrusion (not shown).

The joint prosthesis assembly 510 also includes a magnetic prosthesis (not shown). In at least one example embodiment, the magnetic prosthesis is inserted or welded in the recess. In another example embodiment, the magnetic prosthesis is inserted or welded in the first prosthesis 511, and the recess is formed in the magnetic prosthesis. In yet another example embodiment, the magnetic prosthesis may be disposed on the protrusion and couple into the recess of the first prosthesis 511. The marker on the first prosthesis 511 and the marker (not shown) on the second prosthesis 515 may be utilized to ensure proper alignment during an implant procedure.

It will be appreciated that FIGS. 5A and 5B pertain to embodiments similar to the embodiments of FIGS. 1-4B. For example, the structure and function of the first prosthesis, the recess, the marker of the first prosthesis, the magnetic prosthesis, the second prosthesis, the protrusion, the stem portion, and the marker of the second prosthesis in FIGS. 5A and 5B are the same or similar to those of the first prosthesis, the recess, the marker of the first prosthesis, the magnetic prosthesis, the second prosthesis, the protrusion, the stem portion, and the marker of the second prosthesis in FIGS. 1-4B.

FIGS. 6A-6C show implantable a joint prosthesis assembly 600 (in different view) for joint arthroplasty having a side loading mechanism with a screw locking mechanism, according to at least some example embodiments.

The joint prosthesis assembly 600 includes a first prosthesis 601 and a second prosthesis 605. The first prosthesis 601 includes a recess 602 and a marker (not shown). The second prosthesis 605 includes a stem portion 607 and a protrusion 606. The joint prosthesis assembly 600 also includes a magnetic prosthesis 604. In at least one example embodiment, the magnetic prosthesis 604 is inserted or welded in the recess 602. In another example embodiment, the magnetic prosthesis 604 is inserted or welded in the first prosthesis 601, and the recess 602 is formed in the magnetic prosthesis 604. In yet another example embodiment, the magnetic prosthesis 604 may be disposed on the protrusion 606 and couple into the recess 602 of the first prosthesis 601. The marker on the first prosthesis 601 and the marker (not shown) on the second prosthesis 605 may be utilized to ensure proper alignment during an implant procedure.

It will be appreciated that FIGS. 6A-6C describes embodiments similar to the embodiments of FIGS. 1-5B. For example, the structure and function of the first prosthesis, the recess, the marker of the first prosthesis, the magnetic prosthesis, the second prosthesis, the protrusion, the stem portion, and the marker of the second prosthesis in FIGS. 6A-6C are the same or similar to those of the first prosthesis, the recess, the marker of the first prosthesis, the magnetic prosthesis, the second prosthesis, the protrusion, the stem portion, and the marker of the second prosthesis in FIGS. 1-5B.

The protrusion 606 includes a peg 606a and a collar 606b. As shown in FIGS. 6A-6C, the collar 606b is a disc shape with a height (e.g., about 1 mm), and may be of any suitable shape (e.g., rod, etc., to match the shape of the recess 602) and may have any suitable height to restore radial length. The first prosthesis 601 (e.g., a radial head) may be configured to be angled and smooth to improve contact with e.g., a radial notch. The first prosthesis 601 may be highly polished to maintain articulation. The height of the first prosthesis 601 may range from about 10 mm to about 11.5 mm (if including the collar 606b height which is about 1 mm, the total height would range from about 11 mm to about 12.5 mm). The height of the collar 606b may vary to restore radial length. The diameter (of a top surface) of the first prosthesis 601 may be about 18 mm. The protrusion 606 may have a contoured lateral surface to improve interface with e.g., the annular ligament. The stem portion 607 may be fluted for rotational stability. The stem portion 607 may have grit-blasted surface to promote bony on-growth. The stem portion 607 may have a length of about 25 mm, which may be long enough to provide stability against bending movement but short enough not to reach e.g., the bend in the proximal canal. The stem portion 607 may have a tapered (e.g., triangle-shaped) end to aid insertion.

The first prosthesis 601 includes a side opening 690, which connects to the recess 602 and is configured to allow the peg 606a to slide into the recess 602. The peg 606a may have notches 694 on two opposite sides. The side opening 690 is shaped corresponding to the notches 694 of the peg 606a to facilitate the sliding of the peg 606a into the recess 602 and to prevent vertical movement of the peg 606a relative to the first prosthesis 601. On a side opposite to the side opening 690, the first prosthesis 601 includes a hole 691. The hole 691 connects to the recess 602 and is configured to allow a screw 692 to pass into the recess 602.

The screw 692 may be a locking screw or a set screw to connect/couple the first prosthesis 601 with the peg 606a. It will be appreciated that using the screw fixation/mechanism alone may not be reliable; pitfalls include accidental cross threading of the screw(s) into the prosthesis and eventual loosening of the screw(s) over time. The screw(s) may also strip from over tightening. Moreover, the screw head(s) may shear off the shaft. With the screw fixation/mechanism alone, loosening or cross threading of the screw(s) may be a concern. For example, if the articulation is off or loosens, progressive loosening may occur with ultimate complete disarticulation. The magnet locking mechanism disclosed herein may be used in conjunction with screw(s) to prevent loosening or backing out of joint articulations.

The peg 606a includes a screw-hole 693. The screw-hole 693 is disposed at a side that is perpendicular to the sides of the notches 694. In an operation, the side having the screw-hole 693 is facing the opening 690, and the first prosthesis 601 is sliding toward the peg 606a of the second prosthesis 605. The peg 606a passes through the opening 690 and is then housed in the recess 602. This process is defined as side-loading (of the first prosthesis 601 onto the second prosthesis 605).

It will be appreciated that the first prosthesis 601 may include engagement grooves (not shown) on the sides (e.g., the symmetric two sides that is typically perpendicular to the side where the opening 690 (or the hole 691) is located) of the first prosthesis 601, to engage with an alignment tool (not shown, to align the marker of the first prosthesis 601 with the marker of the second prosthesis 605) that is used to control the position of the first prosthesis 601.

When the first prosthesis 601 is side-loaded onto the second prosthesis 605, the hole 691 may be aligned with the screw-hole 693, and the magnetic prosthesis 604 may lock the first prosthesis 601 and the second prosthesis 605 in place (a click may be audible when the magnet attaches to the ferromagnetic metal). Bone holding forceps may be used in the procedures such as resecting a portion of the joint, preparing a medullary canal of the joint, and/or inserting a second prosthesis of the joint prosthesis assembly into the medullary canal, etc. to hold the bone/joint. After removing the bone holding forceps, the alignment tool may be secured to the first prosthesis 601 by engaging with the grooves of the first prosthesis 601, and to control the position of the first prosthesis 601 so that the hole 691 is disposed laterally to allow easy access to the surgeon. The alignment tool may also be used to align the marker of the first prosthesis 601 with the marker of the second prosthesis 605. The screw 692 may be screwed into the screw-hole 693 via the hole 691 and/or the recess 602 to lock the first prosthesis 601 into the peg 606*a* of the second prosthesis 605.

In a specific example embodiment, the implantable joint prosthesis assembly includes an anatomic radial head made of a durable material (cobalt-chrome and/or other metal alloys) with a rare-earth magnet inserted inside the hollowed radial head shell. The magnet has a recess in the middle that may be square, rectangular, circular, etc. in shape. A prosthetic/radial stem with its collar and/or peg that is a ferromagnetic metal of the same matching shape (as the recess) may couple into the magnet. The radial head, the prosthetic stem, and the magnet may be connected by the polarity of the rare-earth magnet pulling (e.g., about 90 newton to about 200 newton strength in a 3 cm diameter magnet disc/rod) the ferromagnetic metal into the recess for the prosthetic stem. The prosthetic stem may be a grit-blast material with plasma coating or a polished smooth stem. The collar and/or peg on the prosthetic stem may be articular with the radial head. The prosthetic stem may be straight or curved in shape with varying lengths. The magnet may be linked to the radial head or the prosthetic stem either by direct magnetic bond or welded to any one of them.

In at least one example embodiment, in performing joint arthroplasty (e.g., implanting the implantable joint prosthesis assembly disclosed herein), an exposure (e.g., cutting and/or opening the skin and the joint capsule) of the joint (e.g., a radiocapitellar joint) of a patient is performed. A portion of the joint (e.g., the radial head, which needs to be replaced) is resected. A medullary canal (e.g., of the proximal radius) is prepared. The second prosthesis (e.g., a radial stem) of the implantable joint prosthesis assembly is inserted into the medullary canal. After appropriate trialing of the size of the first prosthesis (e.g., a radial head) of the implantable joint prosthesis assembly with respect to the height and diameter of the first prosthesis (that matches the resected head of the joint), the first prosthesis is inserted/implanted. The first prosthesis may be inserted from a lateral side of the joint (e.g., the elbow). The magnetic pull (because of the magnet prosthesis of the implantable joint prosthesis assembly interacts with the ferromagnetic metal of the first/second prosthesis) may then allow for the first prosthesis and the second prosthesis to lock into place. The recess in the first prosthesis may allow for reproducible and strong connection between the first prosthesis and the second prosthesis. A surgeon may feel a definite click or lock to ensure that the coupling is complete. As the magnet may pull on the ferromagnetic metal of the first/second prosthesis, the coupling may automatically articulate to its tightest fit. The joint capsule and the skin may then be closed. It will be appreciated that coating of the first prosthesis and/or the second prosthesis of the joint prosthesis assembly with a ferromagnetic metal may be needed to achieve/strength the magnetic pull.

Embodiments disclosed herein may provide (1) secure magnetic bond between components of an implantable joint prosthesis assembly, (2) longevity of the bond, and (3) ease and reproducibility of use. Embodiments disclosed herein may also be used in minimally invasive joint arthroplasty as the articulation does not require impaction. The rare-earth magnets disclosed herein may be combined with, coupled or inserted into any existing metal joint prosthesis without significant alterations to the implant design. Magnets may retain their properties for more than 100 years that may outlast the patient's lifespan. In a magnetic locking or coupling mechanism disclosed herein, if there is slight shifting of the prosthesis from impaction, the magnet and ferromagnetic metal may seek to re-bond and articulate back in place without intervention.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Different features, variations and multiple different embodiments have been shown and described with various details. What has been described in this application at times in terms of specific embodiments is done for illustrative purposes only and without the intent to limit or suggest that what has been conceived is only one particular embodiment or specific embodiments. It is to be understood that this disclosure is not limited to any single specific embodiments or enumerated variations. Many modifications, variations and other embodiments will come to mind of those skilled in the art, and which are intended to be and are in fact covered by both this disclosure. It is indeed intended that the scope of this disclosure should be determined by a proper legal interpretation and construction of the disclosure, including equivalents, as understood by those of skill in the art relying upon the complete disclosure present at the time of filing.

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:
1. An implantable joint prosthesis assembly for joint arthroplasty, the joint prosthesis assembly comprising:
   a first prosthesis having a recess;
   a second prosthesis having a protrusion; and a magnetic prosthesis configured to connect the first prosthesis of the joint prosthesis assembly to the second prosthesis of the joint prosthesis assembly, wherein the recess is configured to house the protrusion,
the magnetic prosthesis is disposed between the first prosthesis of the joint prosthesis assembly and the second prosthesis of the joint prosthesis assembly,
the first prosthesis is a radial head, the second prosthesis is a radial stem, the radial stem is coated with a ferromagnetic metal.

2. The joint prosthesis assembly according to claim 1, wherein the magnetic prosthesis is a rare-earth magnet.

3. The joint prosthesis assembly according to claim 1, wherein the magnetic prosthesis is inserted in the recess of the radial head.

4. The joint prosthesis assembly according to claim 1, wherein the magnetic prosthesis is welded in the recess of the radial head.

5. The joint prosthesis assembly according to claim 1, wherein the radial head comprises a cobalt-chrome alloy.

6. The joint prosthesis assembly according to claim 1, wherein the magnetic prosthesis is disposed on the protrusion of the radial stem.

7. The joint prosthesis assembly according to claim 1, wherein the magnetic prosthesis is welded on the protrusion of the radial stem.

8. An implantable joint prosthesis assembly for joint arthroplasty, the joint prosthesis assembly comprising:
a first prosthesis having a recess;
a second prosthesis having a protrusion; and
a magnetic prosthesis configured to connect the first prosthesis of the joint prosthesis assembly to the second prosthesis of the joint prosthesis assembly, wherein the recess is configured to house the protrusion,
the magnetic prosthesis is disposed between the first prosthesis of the joint prosthesis assembly and the second prosthesis of the joint prosthesis assembly,
the first prosthesis is a radial head having a side opening that is connected to the recess and forming a groove that is configured to allow the protrusion to slide into the recess via the groove.

9. An implantable joint prosthesis assembly for joint arthroplasty, the joint prosthesis assembly comprising:
a first prosthesis having a recess;
a second prosthesis having a protrusion; and
a magnetic prosthesis configured to connect the first prosthesis of the joint prosthesis assembly to the second prosthesis of the joint prosthesis assembly,
wherein the recess is configured to house the protrusion,
the magnetic prosthesis is disposed between the first prosthesis of the joint prosthesis assembly and the second prosthesis of the joint prosthesis assembly,
wherein the second prosthesis is a radial stem comprising a grit-blast material with plasma coating.

10. An implantable joint prosthesis assembly for joint arthroplasty, the joint prosthesis assembly comprising:
a first prosthesis having a recess;
a second prosthesis having a protrusion; and
a magnetic prosthesis configured to connect the first prosthesis of the joint prosthesis assembly to the second prosthesis of the joint prosthesis assembly,
wherein the recess is configured to house the protrusion,
the magnetic prosthesis is disposed between the first prosthesis of the joint prosthesis assembly and the second prosthesis of the joint prosthesis assembly,
wherein the first prosthesis is a radial head, the second prosthesis is a radial stem, a marker of the radial head is configured to align with a marker of the radial stem.

11. An implantable joint prosthesis assembly for joint arthroplasty, the joint prosthesis assembly comprising:
a first prosthesis having a recess;
a second prosthesis having a protrusion;
a magnetic prosthesis configured to connect the first prosthesis of the joint prosthesis assembly to the second prosthesis of the joint prosthesis assembly; and
a locking screw, wherein
the recess is configured to house the protrusion,
the magnetic prosthesis is disposed between the first prosthesis of the joint prosthesis assembly and the second prosthesis of the joint prosthesis assembly, and
the first prosthesis is a radial head, the second prosthesis is a radial stem, the locking screw is configured to connect the radial head to the protrusion of the radial stem.

12. The joint prosthesis assembly according to claim 11, wherein the radial head has a side opening, the side opening connected to the recess and forming a groove,
wherein the groove is configured to allow the protrusion to slide into the recess via the groove, the locking screw is configured to insert from a side of the radial head opposite to the side opening.

* * * * *